US011618889B2

(12) United States Patent
 Kwon

(10) Patent No.: US 11,618,889 B2
(45) Date of Patent: Apr. 4, 2023

(54) ***SACCHAROMYCES CEREVISIAE* KWON P-1, 2, 3 WHICH PRODUCE ALDEHYDE DEHYDROGENASE AND GLUTATHIONE**

(71) Applicant: PICOENTECH Co., LTD., Seongnam-Si (KR)

(72) Inventor: Hung Taeck Kwon, Seoul (KR)

(73) Assignee: PICOENTECH Co., LTD., Seongnam-Si (KR)

( * ) Notice: Subject to any disclaimer, the term of this patent is extended or adjusted under 35 U.S.C. 154(b) by 0 days.

(21) Appl. No.: 17/176,365

(22) Filed: Feb. 16, 2021

(65) Prior Publication Data

US 2021/0254023 A1   Aug. 19, 2021

(30) Foreign Application Priority Data

Feb. 18, 2020 (KR) ........................ 10-2020-0019858

(51) Int. Cl.
 *C12N 9/02* (2006.01)
 *C12N 1/18* (2006.01)
 *C12N 15/01* (2006.01)
 *C12P 21/02* (2006.01)
 *C12R 1/865* (2006.01)

(52) U.S. Cl.
 CPC ........... *C12N 9/0008* (2013.01); *C12N 1/185* (2021.05); *C12N 15/01* (2013.01); *C12P 21/02* (2013.01); *C12Y 102/01003* (2013.01); *C12R 2001/865* (2021.05)

(58) Field of Classification Search
 CPC ...... C12N 9/0008; C12N 1/185; C12N 15/01; C12R 2001/865; C12P 21/02; C12Y 102/01003
 See application file for complete search history.

(56) References Cited

PUBLICATIONS

Gasent-Ramírez, "Lysine-overproducing mutants of *Saccharomyces cerevisiae* baker's yeast isolated in continuous culture.". Appl Environ Microbiol. Dec. 1997; 63(12): 4800-4806. Retrieved <URL: https://www.ncbi.nlm.nih.gov/pmc/articles/PMC168803/> (Year: 1997).*

Murata, "Phenotype character of the methylglyoxal resistance gene in *Saccharomyces cerevisiae*: expression in *Escherichia coli* and application to breeding wild-type yeast strains". Appl Environ Microbiol. Nov. 1985; 50(5): 1200-1207. Retrieved <URL: https://www.ncbi.nlm.nih.gov/pmc/articles/PMC238725/> (Year: 1985).*

Tahmasebi, "Isolation of indigenous Glutathione producing *Saccharomyces cerevisiae* strains". Iran J Pathol. 2016 Fall; 11(4): 354-362. Retrieved <URL: https://www.ncbi.nlm.nih.gov/pmc/articles/PMC5563933/> (Year: 2016).*

Mezzetti, "Evolved *Saccharomyces cerevisiae* wine strains with enhanced glutathione production obtained by an evolution-based strategy". FEMS Yeast Research, vol. 14, Issue 6, Sep. 2014, pp. 977-987. Retrieved <URL: https://academic.oup.com/femsyr/article/14/6/977/522326> (Year: 2014).*

Oh, "Effects of overexpression of acetaldehyde dehydrogenase 6 and . . . *Saccharomyces cerevisiae*". Biocatalysis and Ag Biotech, vol. 1, Iss 1, Jan. 2012, pp. 15-19.Retrieved <URL: https://www.sciencedirect.com/science/article/pii/S1878818111000120?via%3Dihub> (Year: 2012).*

NITE NBRC, "*Saccharomyces cerevisiae* Kyokai No. 7". Wayback Machine <URL: https://web.archive.org/web/20150906192637/https://www.nite.go.jp/en/nbrc/genome/project/annotation/sc1.html> (Year: 2015).*

Wang, Zheng, Liyang Zhang, and Tianwei Tan. "Efficient screening a high glutathione-content mutant of *Saccharomyces cerevisiae* by flow cytometry." Process Biochemistry 45.7 (2010): 1168-1171. (Year: 2010).*

Murata, Kousaku, and Akira Kimura. "Relationship between glutathione contents and generation times in *Saccharomyces cerevisiae*." Agricultural and biological chemistry 50.4 (1986): 1055-1056. (Year: 1986).*

\* cited by examiner

*Primary Examiner* — Robert J Yamasaki
(74) *Attorney, Agent, or Firm* — Maier & Maier, PLLC

(57) ABSTRACT

A yeast strain producing glutathione (GSH) and aldehyde dehydrogenase, and more specifically, the yeast strains *Saccharomyces cerevisiae* Kwon P-1 KCTC13925BP, *Saccharomyces cerevisiae* Kwon P-2 KCTC14122BP, and *Saccharomyces cerevisiae* Kwon P-3 KCTC14123BP, which produce both glutathione and aldehyde dehydrogenase.

6 Claims, 6 Drawing Sheets

SACCHAROMYCES CEREVISIAE KWON P-1, 2, 3 WHICH PRODUCE ALDEHYDE DEHYDROGENASE AND GLUTATHIONE

TECHNICAL FIELD

The present disclosure relates to a yeast strain producing glutathione (GSH) and aldehyde dehydrogenase. More specifically, the present disclosure relates to the yeast strains *Saccharomyces cerevisiae* Kwon P-1 KCTC13925BP, *Saccharomyces cerevisiae* Kwon P-2 KCTC14122BP, and *Saccharomyces cerevisiae* Kwon P-3 KCTC14123BP, which produce both glutathione and aldehyde dehydrogenase.

BACKGROUND

Glutathione (γ-L-glutamyl-L-cysteinylglycine, GSH), which is a biologically active substance present in cells, is a tripeptide composed of three amino acids: glutamate, cysteine, and glycine. Glutathione is present at a concentration of 0.1-10 mM in the cells of animals, plants, and microorganisms, and accounts for 90% or more of the total non-proteinaceous active components of the cell.

Glutathione has been known to serve as an important antiviral agent in vivo by enhancing immune activity through leukocytogenesis. Glutathione acts as a substrate for glutathione S-transferase (GST) to bind to toxic substances, such as xenobiotics, which are harmful to the living body, in a conjugated form, thereby playing a key role in detoxification.

Glutathione also serves to prevent the damage and necrosis of cell membranes, nucleic acids, and cell structures caused by oxidation in cells and to mitigate toxicity of reactive oxygen species (ROS), a cause of aging. Reactive oxygen species are formed during various biological metabolisms, including superoxides, peroxides, hydroxy radicals, and the like, and are classified into endogenous reactive oxygen species generated from biological metabolites of substances and exogenous reactive oxygen species resulting from tobacco, radioactivity, and the like.

Oxidative stress due to reactive oxygen species may impair cognitive function (Liu et al. 2002), destroy sperm DNA to cause male infertility (Wright et al. 2014), damage cellular proteins, lipids, and nucleic acids to cause cancer, and lower physiological functions to act as a causative factor of various diseases and aging. Therefore, antioxidants that serve to perform disease prevention, immunity enhancement, aging prevention, and the like are very important in our body, and the functions of glutathione, which acts as an antioxidant in cells, are receiving attention in many medical fields including enzymology, pharmacology, therapies, toxicology, endocrinology, and microbiology.

This glutathione is basically synthesized in the body, but with the progress of abnormal conditions, such as disease occurrence, lowered immunity, and aging, the absolute content of glutathione decreases in the human body, resulting in deterioration in health. Therefore, the glutathione supplied from the outside can remove reactive oxygen species in cells to maintain health and slow down aging.

Owing to these physiologically active factors of glutathione in the human body, glutathione is currently used for food, cosmetics, feeds, and pharmaceuticals, and the usage thereof is increasing.

Glutathione is currently produced using edible microorganisms, but the inherent content of glutathione that can be produced from microorganisms is very low, and thus studies are being actively conducted to mass-produce glutathione through high-content glutathione-producing strains by increasing the glutathione content of microorganisms through mutation and recombination technology and applying this technology to fermentation techniques.

Therefore, the development of high-content glutathione-producing strains is attained by developing a fundamental material that increases economic values, and thus allows glutathione to have market competition so as to be used in a broad range of health foods, pharmaceuticals, feeds, and the like. However, the strain development by genetic recombination technology cannot be free from the GMO discussion, which is currently an issue, and thus the scope of use thereof is restricted, but the strain breeding by mutation technology is not restricted in use and thus can be broadly used for various purposes. Therefore, the breeding of high-content glutathione-producing strains through mutation technology is a very important technique.

In Korea, the consumption of alcohol used for drinking is increasing rapidly together with economic growth, and thus national health care is an important issue, and excessive consumption of alcohol is emerging as a major social problem in national health, social, and economic aspects. According to the survey results by the Ministry of Health and Welfare and the Korea Centers for Disease Control and Prevention, in 2016, about 75% of adults over 20 years of age in Korea were reported to consume alcohol at least once a month, and the rate has been increasing every year. In addition, as a result of the WHO survey on country-specific alcohol consumption, the average alcohol consumption of the people over 15 years of age in Korea is 11.9 L per person is higher by 4.8 L than the average alcohol consumption in the world and ranked 17th in the world and first in the Western Pacific Region.

In particular, among Koreans, excessive aldehyde residues in the body, produced by alcohol intake, have been reported to cause diseases resulting from oxidation, such as cardiovascular diseases, diabetes, neurodegenerative diseases, upper digestive and respiratory tract cancers, radiation dermatitis, Fanconi anemia, peripheral nerve damage, inflammation, osteoporosis, and aging (Chen et al. 2014).

In addition, the scale of social and economic losses due to drinking are reported to amount to about 0.5-2.7% of GDP in most countries. In Korea, it was reported that the social and economic cost due to drinking in 2000 was estimated to be 14.9352 trillion won, of which 6.2845 trillion won was estimated to result from the productivity reduction and the losses due to diseases, accidents, and hangovers (Jung Woo-Jin et al. 2006).

In order to solve these social problems, research and experiments on many substances capable of reducing toxicity of ethanol or inhibiting expression of toxicity thereof are being conducted, leading to the development of various health supplement-related goods. The alcohol entering the body is absorbed into the stomach or small intestine to enter the blood vessels, transferred to the liver, and decomposed and detoxified therein.

Alcohol dehydrogenase (ADH) present in hepatocytes first oxidizes alcohol into acetaldehyde, and the acetaldehyde is again decomposed into acetic acid by acetaldehyde dehydrogenase (ALDH) in hepatocytes, and then acetic acid is transferred to muscles and adipose tissues in the body and finally decomposed into carbonic acid gas and water. Acetaldehyde, the first metabolite of ethanol, is the main cause of hangovers and alcoholic liver disorders due to very high reactivity and strong toxicity compared with ethanol.

Humans have been reported to retain 19 types of aldehyde dehydrogenase (Marchitti et al. 2007, 2008), among which, as a result of enzymatic engineering, acetaldehyde dehydrogenase 2 which is mainly present in mitochondria, when analyzed using acetaldehyde as an enzymatic substrate, showed the lowest Km value (up to 0.2 µM) compared with when the other types of aldehydes were used as substrates, indicating that acetaldehyde dehydrogenase 2 most favorably oxidizes and removes acetaldehyde derived from alcohol.

Since acetaldehyde, a hangover causing substance produced in the in vivo ethanol metabolism, is most effectively converted to acetic acid, the removal of aldehydes is very important for human health (Eriksson et al. 1977 and Klyosov et al. 1996-1). In addition, aldehyde dehydrogenase 2 is used in the metabolism of not only acetaldehyde but also aldehydes, such as aliphatic aldehydes, aromatic aldehydes, and polycyclic aldehydes, to remove toxic substances in the body (Klyosov et al. 1996-2).

As a representative example, aldehyde dehydrogenase 2 serves to remove 4-hydroxy-2-nonenal (4-HNE) and malondialdehyde (MDA), which are oxidized aldehydes generated during oxidative stress, and to remove acrolein generated from cigarette smoke and automobile exhaust fumes (Chen et al. 2010 and Yoval-Sanchez et al. 2012). The persons who have a little expression of aldehyde dehydrogenase 2 in the human body or have a mutation of glutamic acid to lysine at the 487th amino acid residue of this enzyme not only show a sensitive response, such as facial flushing, to even a small amount of alcohol, but also have a high concentration of acetaldehyde in the blood when drinking, due to poor conversion. (Yoshida et al. 1984).

In particular, the persons who have ALDH2-2, a homozygote for aldehyde dehydrogenase 2, are known through many studies as being susceptible to drinking, and such a genetic variation is little shown in Westerners but is found in 50% of the total population in Koreans, Chinese, and Japanese. (Brooks et al. 2009).

Regarding the research and development of aldehyde dehydrogenase 2, aldehyde dehydrogenase 2 promoters and inhibitors in the body are actively studied for medical purposes, and thus the importance of aldehyde dehydrogenase 2 is emphasized (Budas et al. 2009, Chen et al. 2014, and M.zel et al. 2018), but research on the development of breeding or mass-production of microorganisms producing a high content of aldehyde dehydrogenase 2 is not still sufficient.

Regarding the development of strains producing aldehyde dehydrogenase 2 with high efficiency, it has been reported that a protein expression system using *E. coli* as a host was used to express human aldehyde dehydrogenase 1 and 2 proteins, of which only 30% were expressed as an active soluble enzyme to thereby produce only 2-4 mg/L of protein (Zheng et al. 1993). It has been reported that 95% of rat aldehyde dehydrogenase 2 was expressed as an active soluble protein, but a very little protein, 1-2 mg/L, was produced (Jeng et al. 1991).

However, there has no report of cases in which the production of aldehyde dehydrogenase is increased by using a mutation method which is easy to utilize due to small legal restrictions. Therefore, for the enlargement of the range of use of aldehyde dehydrogenase, the development of microorganisms having highly active aldehyde dehydrogenase by a mutation method is urgently needed.

In general, gene recombination technology, mutation technology, or the like is widely used in strain breeding for increasing productivity of target products from microbial strains, but strain modification by genetic recombination technology has many legal limiting factors and has limitations in the scope of application, and therefore, a mutation induction method is very advantageous.

As for the mutation induction method for strain modification, mutation is generally induced in strain genes by using a chemical substance, such as ethylmethanesulfonate (EMS) or methylnitronitrosoguanidine (NTG), ultraviolet (UV) light, or the like, to change strain characteristics, and then selection factors suitable for the production of target products are applied thereto to implement adaptation of desired traits, thereby inducing and selecting desired mutants.

In biological genes, guanine pairs with cytosine via triple hydrogen bonds and adenine pairs with thymine via double hydrogen bonds, and gene nucleotide sequences storing genetic information are configured such that guanine necessarily pairs with cytosine and adenine necessarily pairs with thymine due to triple and double hydrogen bonds therebetween.

When a chemical substance is used as a mutagen, for example, when the chemical mutagen EMS or NTG is mainly used, O-6-ethyl guanine is formed by guanine alkylation, eventually hindering the formation of triple bonds and finally forming double bonds with thymine, and thus, a gene base pair in this site may be changed.

When DNA replication occurs in a state in which the gene bases are changed, the thymine portion pairs with adenine, and thus the guanine-cytosine site is replaced with the adenine-thymine site (Nahafi et al. 2013), whereby mutation occurs.

In the selection of mutants by adaptation, methylglyoxal is a toxic substance synthesized in the glycolysis and aminoacetone cycle and is converted to lactic acid by glyoxal reductase. Through the property of glutathione to be involved as a coenzyme in this system, a medium containing glyoxal is used to induce strains with high glutathione productivity.

That is, a lack of glutathione renders this system inoperable to result in an increase in sensitivity, and the overproduced glutathione may increase resistance. Resultantly, methylglyoxal can be used as a selection factor for selecting glutathione-overproducing strains (Ohtake et al. 1990 and Hamad et al, 2018).

The mutant derivatives that produce a lot of aldehyde dehydrogenase can be selected by adding lysine to media. Lysine not only inhibits the growth of cells by acting with negatively charged bacterial membranes and then disrupting cell membrane structures, but also inhibits the growth of microorganisms by penetrating into cells and then acting with nucleic acids to inhibit protein synthesis.

Therefore, resistant strains capable of growing in conditions of containing a high concentration of lysine can increase protein synthesis ability, and ultimately, can be used in a method for selecting aldehyde dehydrogenase-overproducing strains.

As discussed above, the use of both glutathione and aldehyde dehydrogenase is highly efficient in order to remove chemical substances, such as reactive oxygen species and various aldehydes, among various harmful substances accumulated in the human body, but the development of strains producing both glutathione and aldehyde dehydrogenase was not reported in the investigation so far.

In the present disclosure, strains capable of producing both aldehyde dehydrogenase and glutathione with high efficiency were developed by firstly creating mutant strains through chemical mutation and secondarily selecting selection factor-adapted strains.

A chemical method using ethylmethanesulfonate (EMS) or methylnitronitrosoguanidine (NTG) was firstly used, and secondarily, in the selection, two adaptation tests using methylglyoxal and lysine, which had not been attempted so far, were used to finally select strains overproducing both glutathione and aldehyde dehydrogenase.

Mutant strains overproducing both glutathione and aldehyde dehydrogenase have been reported to be generally recognized as safe (GRAS) in the use of food, health food, feeds, cosmetics, and medicines, and wild *Saccharomyces cerevisiae*, which has already been known to produce both glutathione and aldehyde dehydrogenase, albeit with low production efficiency, was selected and used.

As such, *Saccharomyces cerevisiae* sp., which is a novel modified strain having both an enhanced ability to produce glutathione and an enhanced ability to produce aldehyde dehydrogenase, was secured through mutation, and therefore, the present disclosure has been completed.

SUMMARY

The object of the present invention is to provide the mutant yeast strain, *Saccharomyces cerevisiae* Kwon P-1 KCTC13925BP, *Saccharomyces cerevisiae* Kwon P-2 KCTC14122BP and *Saccharomyces cerevisiae* Kwon P-3 KCTC14123BP, having an excellent ability to produce both glutathione and aldehyde dehydrogenase.

The wild yeasts selected on the basis of the above standard were artificially chemically mutated, and then glutathione-overproducing strains were selected by a methylglyoxal-adapted mutant strain selecting method and aldehyde dehydrogenase-overproducing strains were selected by a lysine-adapted mutant strain selecting method, and finally, *Saccharomyces cerevisiae* overproducing both glutathione and aldehyde dehydrogenase were selected.

Hereinafter, the mutation induction method and the selected mutant yeasts of the present disclosure will be described in more detail.

As for the mutant strain *Saccharomyces cerevisiae* Kwon P-1 KCTC13925BP, 20 species of strains producing both glutathione and aldehyde dehydrogenase, albeit in small amounts, were selected among 250 species of wild *Saccharomyces cerevisiae* strains isolated from Korean raw rice wine, fermented malt, and the like, and then one species of strain having the highest productivity of both was finally selected.

Thereafter, in order to increase glutathione productivity of mutant microorganisms, which were obtained by inducing chemical mutation in selected 20 species of strains through nitrosoguanidine (NTG) or ethyl-methane-sulfonate (EMS) treatment, resistant yeast microorganisms having high adaptation to methylglyoxal with a concentration of, but not limited to, 5-15 mM and preferably 10 mM, were firstly selected.

Thereafter, as for secondary selection, in order to select novel mutant yeast strains having adapted resistance to lysine for selection of microorganisms having high productivity of aldehyde dehydrogenase, yeast microorganisms having resistance to lysine with a concentration of, but not limited to, 3-5% and preferably 3% were selected. Finally, *Saccharomyces cerevisiae* Kwon P-1 having high productivity of both glutathione and aldehyde dehydrogenase was selected.

*Saccharomyces cerevisiae* Kwon P-1 has been deposited with the international depository under the accession number KCTC13925BP, *Saccharomyces cerevisiae* Kwon P-2 has been deposited with the international depository under the accession number KCTC14122BP and *Saccharomyces cerevisiae* Kwon P-3 has been deposited with the international depository under the accession number KCTC14123BP and characterized by having an excellent ability to produce both glutathione and aldehyde dehydrogenase.

In an embodiment of the present disclosure, as for the mutant strain *Saccharomyces cerevisiae* Kwon P-1 KCTC13925BP, mutation is induced by nitrosoguanidine (NTG) or ethyl-methane-sulfonate (EMS) treatment in strains having an ability to produce both glutathione and aldehyde dehydrogenase, albeit in small amounts, which were selected from wild *Saccharomyces cerevisiae* strains, and then from the selected strains, strains having resistance to methylglyoxal and resistance to lysine were selected, and these strains were verified to have excellent productivity of two substances, glutathione and aldehyde dehydrogenase, compared with the initially selected wild strain.

DETAILED DESCRIPTION OF THE EMBODIMENTS

Hereinafter, constitutions and effects of the present disclosure will be described in more detail with reference to the following examples. However, these examples are used for illustration only, and the scope of the present disclosure is not limited by these examples.

Example 1

Selection of Strains Having Enhanced Ability to Produce Glutathione

In order to select novel mutant strains having an enhanced ability to produce glutathione, the wild *Saccharomyces cerevisiae* strain was treated with ethyl-methane-sulfonate (EMS) or nitrosoguanidine (NTG) for mutation induction, followed by evaluation for resistance to methylglyoxal, thereby finally selecting strains having an enhanced ability to produce glutathione. Specifically, experiments were carried out as follows.

Example 1-1: Analysis of Survival Rate of Wild *Saccharomyces cerevisiae* Strains in Methylglyoxal In order to establish experimental conditions for selecting novel mutant yeast strains having an enhanced ability to produce glutathione, the survival rate was measured to determine the range of the treatment concentration and then the treatment concentration was intended to be selected, before the selection of strains having resistance to methylglyoxal. *Saccharomyces cerevisiae* selected from the wild was used as a mother strain.

Specifically, in order to select resistant strains of mutant strains, the survival rate of the prepared yeast strain was checked for different methylglyoxal treatment concentrations. The strain was seeded in YPD media (2% peptone, 1% yeast extract, 2% glucose) and grown at 30° C. until the $OD_{600\ nm}$ (optical density at 600 nm) value reached 0.5, and then the cells were recovered. The recovered cells were seeded by plating on YPD agar media (with 1.5% agar added) supplemented with methylglyoxal at concentrations of 0 mM, 5 mM, 10 mM and 15 mM, separately, and then cultured. During this procedure, the recovered cells were washed with 0.1 M citric buffer (pH 5.5), and then, the cells were plated on YPD agar media supplemented with methylglyoxal after the $OD_{600\ nm}$ value was adjusted to 1.0. After plating, the cells were cultured at 30° C. for 48 hours, and the survival curve of the strain was plotted on the graph.

Figure 1:
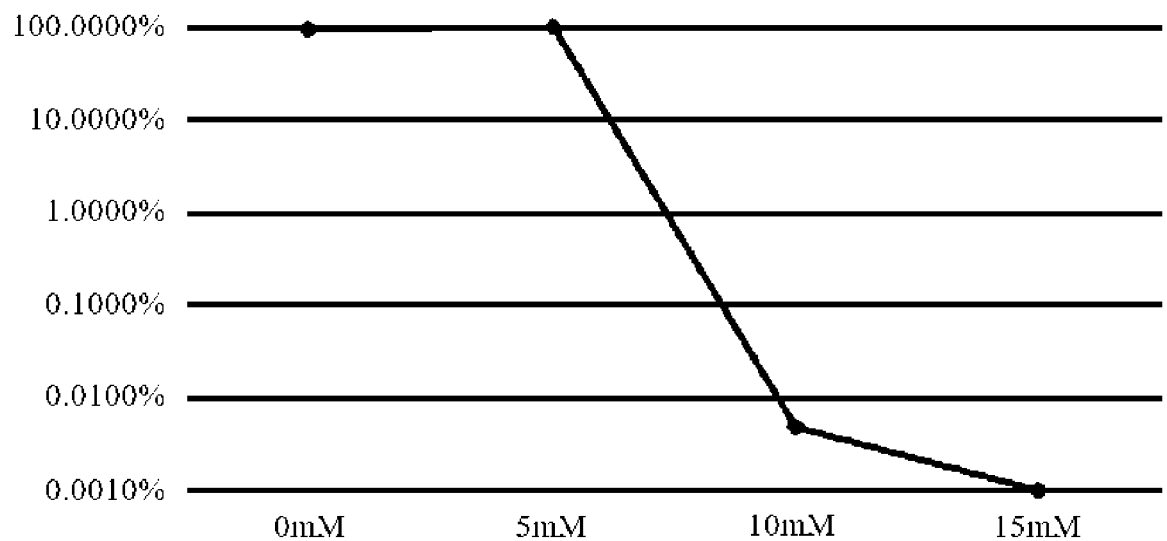
FIG. 1 is a graph showing a curve of survival rate of wild *Saccharomyces cerevisiae* strain versus treatment concentration of methylglyoxal according to an example of the present disclosure.

As shown in the results in FIG. 1, the treatment with 10 mM methylglyoxal resulted in a death rate of 99.995%, and the treatment with 15 mM methylglyoxal resulted in the death of 100% of test microorganisms.

Therefore, in order to select novel mutant strains having an enhanced ability to produce glutathione, YPD agar media supplemented with 10 mM methylglyoxal were used on the basis of the result, so as to select methylglyoxal-resistant strains of the wild strain.

Example 1-2: Establishment of Mutation Conditions for Selecting Candidate Mutant Strains Having Enhanced Ability to Produce Glutathione Experimental conditions for selecting novel mutant strains having an enhanced ability to produce glutathione were established in Example 1-1. Specifically, in order to select methylglyoxal-resistant strains of the wild strain, 10 mM methylglyoxal was added to YPD agar media.

Therefore, in order to select mutant strains having an enhanced ability to produce glutathione from the wild strain, a curve of survival rate versus treatment concentration of ethyl-methane-sulfonate (EMS) or nitrosoguanidine (NTG) was created.

Specifically, the wild strain was seeded in YPD media, and grown until the $OD_{600\ nm}$ value reached 0.5 or for 24 hours. Then, the two types of cultures were centrifuged at 4,000 rpm for 10 minutes to recover precipitated cells. The recovered cells were washed two times with 0.1 M citric buffer (pH 5.5), followed by centrifugation, and finally, the cells were diluted with 0.1 M citric buffer (pH 5.5) until the $OD_{600\ nm}$ value reached 1.0, and then used. Thereafter, for induction of mutation, 0.1 M citric buffers (pH 5.5) containing 1%, 2%, 3%, and 4% NTG were added to the cells recovered after centrifugation, wherein the cells were treated with NTG in a temperature condition of 30° C. for 30 minutes. The NTG-treated mutant strains were centrifuged at 4,000 rpm for 10 minutes to recover the cells, and then the cells were washed two times with 0.1 M citric buffer (pH 5.5). After 1 mL of 0.1 M citric buffer (pH 5.5) was added to and mixed with the washed cells, the mixture was plated on YPD agar media.

Meanwhile, in order to select methylglyoxal-resistant mutant strains by the treatment with EMS, which is a substance for mutation induction, 1 mL of the wild yeast strain grown in the same conditions as in the case of NTG treatment was taken and centrifuged. 0.1 M citric buffers (pH 5.5) containing 1%, 2%, 3%, and 4% EMS were added to the cells recovered after centrifugation, wherein the microorganisms were treated in a temperature condition of 30° C. for 60 minutes. The EMS-treated mutant strains were centrifuged at 4,000 rpm for 10 minutes to recover the cells, and then the cells were washed two times with 0.1 M citric buffer (pH 5.5). After 1 mL of 0.1 M citric buffer (pH 5.5) was added to and mixed with the washed cells, the mixture was plated on YPD agar media.

Figure 2:
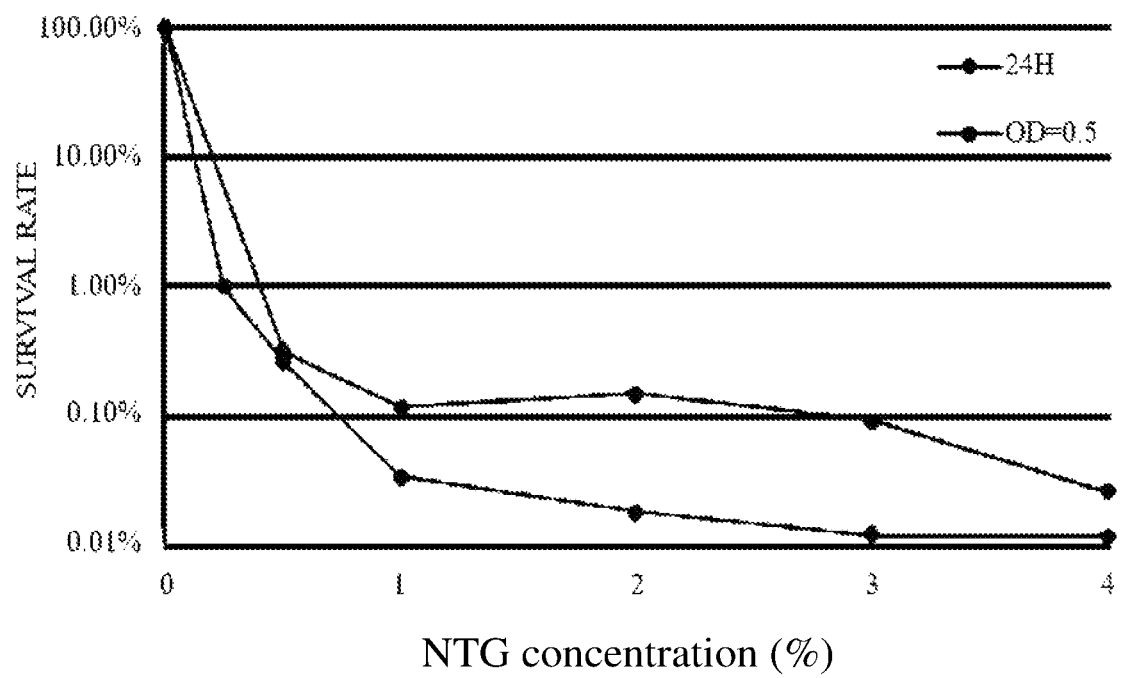
FIG. 2 is a graph showing curves of survival rate of wild *Saccharomyces cerevisiae* strain versus treatment concentration of NTG according to an example of the present disclosure, in which the blue curve represents the survival rate of wild *Saccharomyces cerevisiae* cultured for 24 hours and the orange curve represents the survival rate of wild *Saccharomyces cerevisiae* cultured until the OD value reached 0.5.
Figure 3:
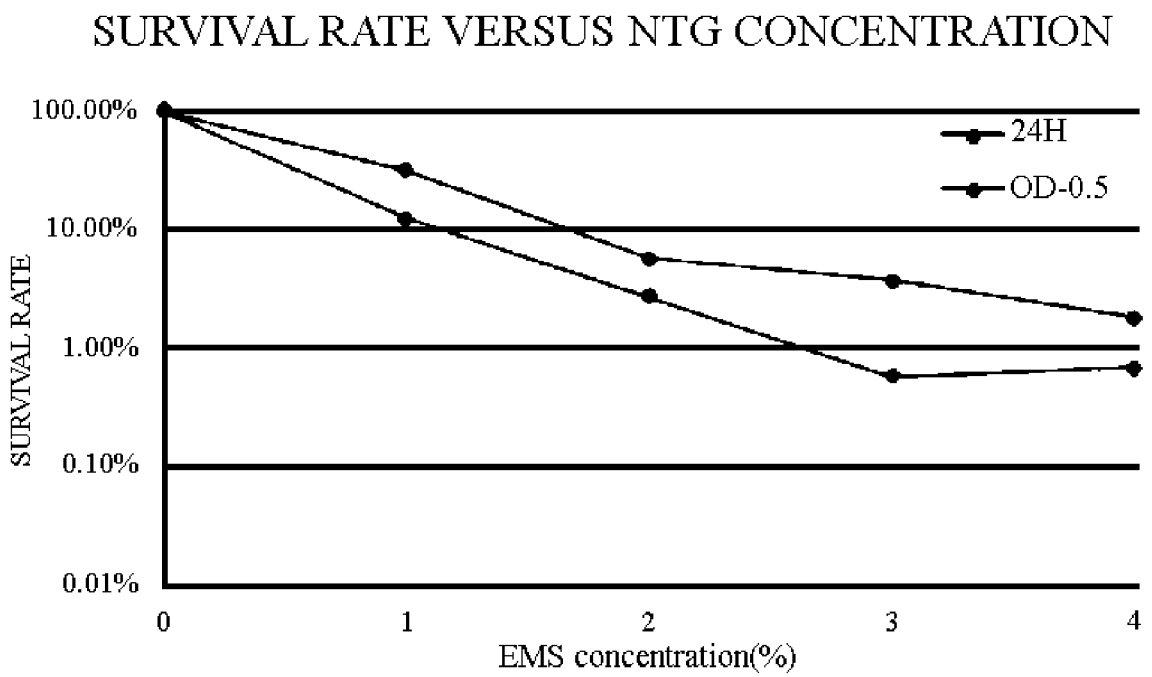
FIG. 3 is a graph showing curves of survival rate of wild *Saccharomyces cerevisiae* strain versus treatment concentration of EMS according to an example of the present disclosure, in which the blue curve represents the survival rate of wild *Saccharomyces cerevisiae* cultured for 24 hours and the orange curve represents the survival rate of wild *Saccharomyces cerevisiae* cultured until the OD value reached 0.5.

As shown in the results of FIG. 3 below, the treatment with 3% EMS after 24-hour culture resulted in a death rate of 99.4%. In addition, as shown in FIG. 2, the treatment with 1% EMS after 24-hour culture resulted in a death rate of 99.7%.

Therefore, in order to select novel mutant yeast strains having an enhanced ability to produce glutathione, the optimal treatment concentrations of NTG and EMS for selecting glutathione-resistant strains of the wild strain were selected to be 1% and 3%, respectively, on the basis of the above results.

Example 1-3: Selection of Candidate Mutant Strains Having Enhanced Ability to Produce Glutathione Experimental conditions for selecting novel mutant yeast strains having an enhanced ability to produce glutathione were established in Example 1-2. Specifically, for the selection of methylglyoxal-resistant strains of the wild yeast strain, methylglyoxal was intended to be added at a concentration of 10 mM to YNB agar media, and for mutation, the conditions of 1% NTG and 3% EMS were established.

Therefore, in order to select mutant strains having an enhanced ability to produce glutathione from the wild strain, methylglyoxal-resistant mutant strains were selected and the cells were grown in YPD media. Then, the concentration of glutathione was measured and expressed as the content of glutathione (%, g/g-cell) in cells.

Specifically, the wild strain was seeded in YPD media and grown for 24 hours, and then the culture was obtained and centrifuged at 4,000 rpm for 10 minutes, thereby recovering cells. Thereafter, the recovered cells were washed two times with 0.1 M citric buffer (pH 5.5), and finally diluted with 0.1 M citric buffer (pH 5.5) until the $OD_{600\,nm}$ value reached 1.0, and then used. For mutation induction, the cells were separately treated with 0.1 M citric buffer (pH 5.5) containing 3% EMS for 10 minutes and 0.1 M citric buffer (pH 5.5) containing 1% NTG for 30 minutes, the mutated microorganisms were centrifuged at 4,000 rpm for 10 minutes to recover cells, 0.1 M citric buffer (pH 5.5) was added and mixed with the cells, and then the mixtures were plated on YPD agar media supplemented with 10 mM methylglyoxal. After plating and culture, the surviving strains were recovered, and cultured in YPD media for 48 hours. As for culture conditions, the culture temperature was 30° C. and the stirring rate was 160 rpm. After the cells were cultured for 48 hours, the concentration of glutathione was measured and expressed as the content of glutathione (%, g/g-cell).

For the analysis of glutathione concentration, the cultured cells were centrifuged, and 1 mL of water was added to the precipitated cells, followed by stirring at 1,000 rpm for 2 hours at 85° C., and then extraction was conducted. After extraction, the cells were removed using a centrifuge, and the supernatant was recovered by filtration through a 0.22 μm-filter. Through HPLC (Shimazu LC-20AD) analysis, the concentration of glutathione contained in the recovered filtrate was measured. The glutathione concentration was analyzed using a standard curve of glutathione, and as for HPLC analysis conditions, a C18 column was used for analysis. A mobile-phase solvent (a mixture of 2.02 g/L sodium 1-heptanesulfonate monohydrate, 6.8 g/L potassium dihydrogen phosphate, and methanol of pH 3.0) was allowed to flow at a flow rate of 1 ml/min, and the concentration of glutathione was determined by detection at a wavelength of 210 nm in an ultraviolet detector.

Figure 4:
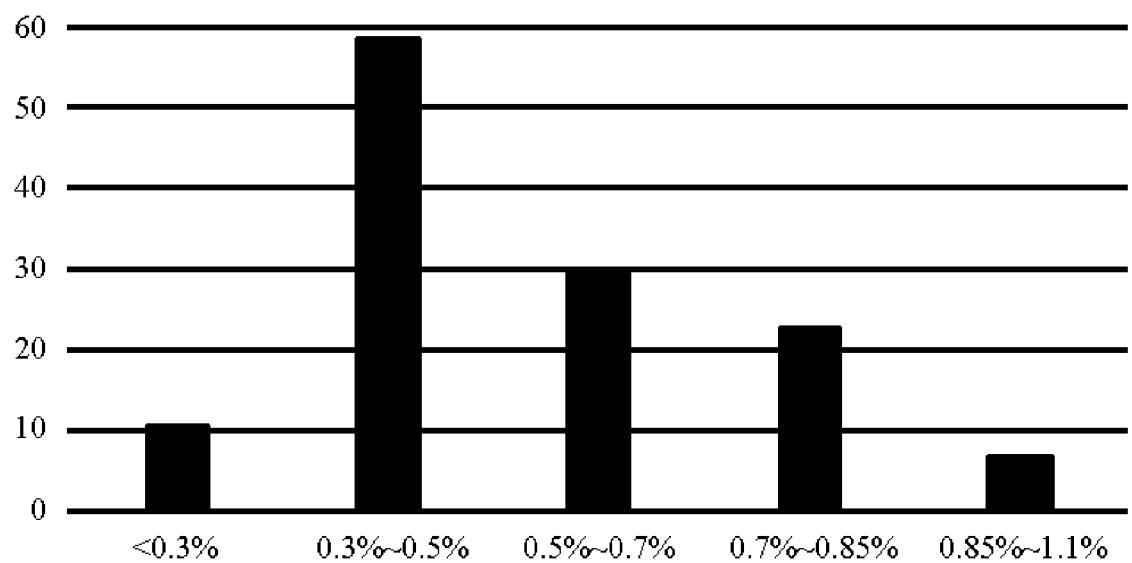
FIG. 4 is a graph showing the concentration distribution results of glutathione produced from *Saccharomyces cerevisiae* mutant strains according to an example of the present disclosure. The horizontal axis represents the glutathione content per cell and the vertical axis represents the number of colonies.

A total of 130 mutant strains were generated, and as a result of analyzing the glutathione concentration of each mutant strain, as shown in FIG. 4, 70 species of mutant strains had a glutathione content of 0.3% to less than 0.5%; 30 species of mutant strains had a glutathione content of 0.5% to less than 0.7%; 23 species of mutant strains had a glutathione content of 0.7% to less than 0.85%; and 7 species of mutant strains had a glutathione content of 0.85% to less than 1.1%. That is, 48.6% of methylglyoxal-resistant strains, which were generated by EMS or NTG treatment, showed an enhanced ability to produce glutathione compared with the glutathione content, which was 42%, in cells of the wild strain, and among such strains, 7 species of mutant strains showed an ability to produce glutathione, enhanced by two times or more compared with mother strains, as shown in Table 1 below.

Based on the above results, *Saccharomyces cerevisiae* ems c7, which had the best glutathione-producing ability among methylglyoxal-resistant mutant strains by EMS treatment, was selected as the final candidate mutant strain having excellent glutathione-producing ability.

Hereinafter, in Example 2 below, the aldehyde dehydrogenase-producing ability of the candidate strains selected using mutation through NTG treatment was enhanced.

TABLE 1

Culture results of methylglyoxal-resistant mutant strains of yeast by EMS or NTG treatment

| No. | Strain name | Mutation treatment method | Glutathione content (%) |
|---|---|---|---|
| Control | *Saccharomyces cerevisiae* WT | — | 0.42 |
| Test group 1 | *Saccharomyces cerevisiae* ems c7 | EMS/methylglyoxal resistance | 0.95 |
| Test group 2 | *Saccharomyces cerevisiae* ems d5 | EMS/methylglyoxal resistance | 0.88 |
| Test group 3 | *Saccharomyces cerevisiae* ems d6 | EMS/methylglyoxal resistance | 0.92 |
| Test group 4 | *Saccharomyces cerevisiae* ems e1 | EMS/methylglyoxal resistance | 0.93 |
| Test group 5 | *Saccharomyces cerevisiae* ems e3 | EMS/methylglyoxal resistance | 0.85 |
| Test group 6 | *Saccharomyces cerevisiae* ntg g6 | NTG/methylglyoxal resistance | 0.86 |
| Test group 7 | *Saccharomyces cerevisiae* ntg h1 | NTG/methylglyoxal resistance | 0.88 |

Example 2

Selection of Strains Having Enhanced Ability to Produce Aldehyde Dehydrogenase (ALDH)

In Order to Select Novel Mutant Strains Having an Enhanced Ability to Produce Aldehyde dehydrogenase, *Saccharomyces cerevisiae* ems c7 showing the highest glutathione production, which was selected in Example 1, was evaluated for resistance to lysine, and finally, strains having an enhanced ability to produce aldehyde dehydrogenase were selected. Specifically, the following experiments were conducted.

Example 2-1: Analysis of Survival Rate of *Saccharomyces cerevisiae* Ems c7 Strain in Lysine To establish experimental conditions for selecting novel mutant strains having an enhanced ability to produce aldehyde dehydrogenase, the optimal lysine treatment concentration for selecting lysine-resistant strains of the glutathione mutant strain *Saccharomyces cerevisiae* ems c7 was intended to be selected. *Saccharomyces cerevisiae* ems c7 having an enhanced ability to produce glutathione was prepared, and this strain was used as a mother strain.

Specifically, in order to select lysine-resistant strains of the *Saccharomyces cerevisiae* mutant strain, the survival rate of the prepared *Saccharomyces cerevisiae* ems c7 strain versus the lysine treatment concentration was checked. To this end, the strain was seeded in YPD media (2% peptone, 1% yeast extract, 2% glucose) and grown at 30° C. until the $OD_{600\,nm}$ value reached 0.5, and then the cells were recovered. The recovered cells were plated on YPD agar media (with 1.5% agar added) supplemented with lysine at concentrations of 0%, 3%, 4%, 5%, 6%, and 7%, separately. The recovered cells were washed with 0.1 M citric buffer (pH 5.5), and then, the cells were plated on YPD agar media supplemented with lysine after the $OD_{600\,nm}$ value was adjusted to 1.0. After plating, the cells were cultured at 30° C. for 48 hours, and a curve of survival rate of the strain was created.

Figure 5:
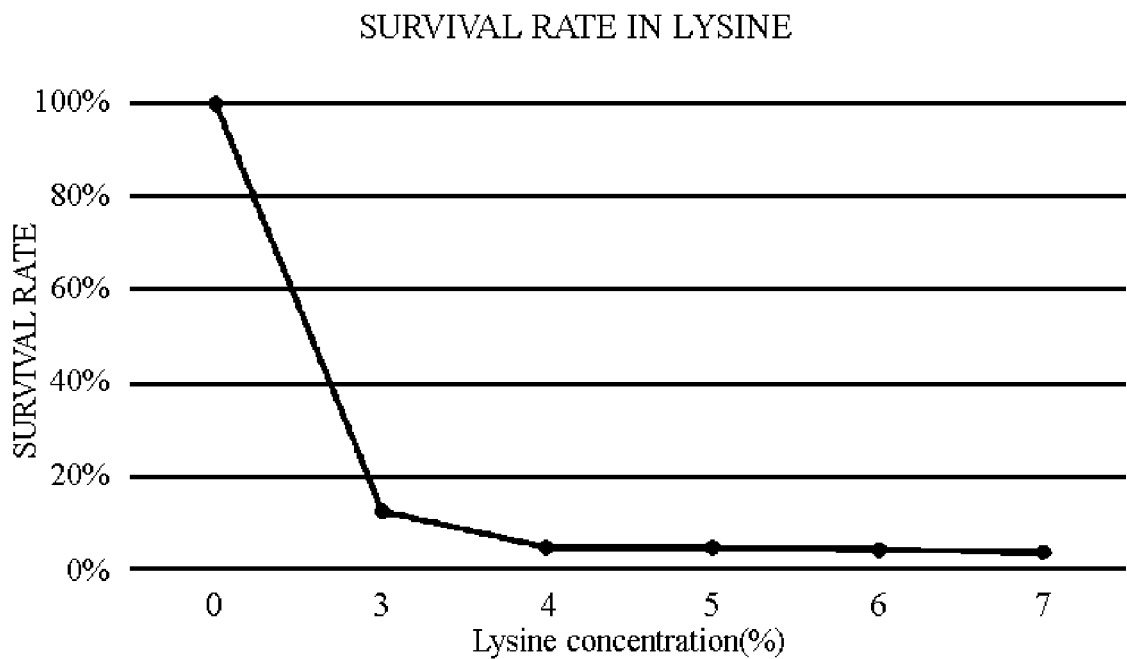
FIG. 5 is a graph showing a curve of survival rate of the wild *Saccharomyces cerevisiae* strain versus treatment concentration of lysine according to an example of the present disclosure.

As shown in the results in FIG. 5, the treatment with 3% lysine resulted in a death rate of 87.5%.

Therefore, in order to select novel mutant strains having an enhanced ability to produce aldehyde dehydrogenase, the optimal lysine treatment concentration for selecting lysine-resistant strains of the *Saccharomyces cerevisiae* ems c7 strain was selected to be 3% on the basis of the above results, and strain selection was carried out by using YPD agar media supplemented with 3% lysine.

Example 2-2: Selection of Candidate Mutant Strains Having Excellent Ability to Produce Aldehyde Dehydrogenase Experimental conditions for selecting novel yeast mutant strains having enhanced aldehyde dehydrogenase activity in Examples 1-2 and 2-1 were established. Specifically, for the selection of lysine-resistant strains of the mutant *Saccharomyces cerevisiae* ems c7 strain, 3% lysine was added to YPD agar media, and for mutation, 1% NTG conditions were established.

Therefore, in order to select mutant strains having an excellent ability to produce glutathione from the *Saccharomyces cerevisiae* ems c7 strain, the cells were grown in YPD media containing 3% lysine and the concentration of aldehyde dehydrogenase was measured.

Specifically, the wild yeast strain was seeded in YPD media and grown for 24 hours, and then the culture was centrifuged at 4,000 rpm for 10 minutes to recover cells. The recovered cells were washed two times with 0.1 M citric buffer (pH 5.5) and diluted by addition of 0.1 M citric buffer (pH 5.5) until the $OD_{600\ nm}$ value reached 1.0. For mutation induction, the cells were treated with 0.1 M citric buffer (pH 5.5) containing 1% NTG for 10 min, and then the mutant strains were centrifuged at 4,000 rpm for 10 minutes to recover cells. Thereafter, 0.1 M citric buffer (pH 5.5) was added and mixed with the cells, and then the mixture was plated on YPD agar media supplemented with 3% lysine. After plating and culture, the surviving strains were recovered, and cultured in YPD media for 48 hours. As for culture conditions, the culture temperature was 30° C. and the stirring rate was 160 rpm. After the cells were cultured for 48 hours, the aldehyde dehydrogenase activity was measured.

However, aldehydes are volatile and are produced in trace amounts, and thus the measurement by an existing method causes a large deviation for the same sample, so that a stable aldehyde measurement method needs to be established. Therefore, the development of new accurate enzyme activity measurement methods based on the above results is absolutely needed in the quality control (QC) of the produced aldehyde dehydrogenase, and thus, a new method was developed in Example 3.

Example 3

Establishment of New Aldehyde Dehydrogenase Activity Measurement Method and Measurement of Enzyme Activity of Mutant Strains As for existing methods for measuring aldehyde dehydrogenase activity, the measurement of NAD(P)+ absorbance at a wavelength of 340 nm was widely used, but this method could not be favorably used since this method checked a change in coenzyme amount and thus corresponds to an indirect method. In order to directly measure the Km value of an enzyme to a substrate of the enzyme, the present inventors employed HPLC analysis for aldehyde quantification. However, the amount of aldehyde consumed by the enzyme ALDH is very small and aldehyde is highly volatile even at room temperature, and thus the direct quantification of aldehyde in the reaction product is technically difficult.

To solve the problem, the present inventors analyzed the amount of aldehyde reduced by the reaction of aldehyde dehydrogenase, on the basis of the reference document (Guan. et. al, 2012) describing that when dinitrophenylhydrazine (DNPH) is added to aldehyde at a certain ratio and reacted at certain concentrations, aldehyde-hydrazone (AcH-DNPH) is formed, and this compound is developed on C18 column for HPLC using acetonitrile as a mobile phase and water as a solvent and thus can be detected and quantified at 360 nm. As for an enzyme reaction solution, 1 mM NADP+ as an enzyme cofactor was added to 50 mM potassium phosphate buffer (pH 8.0), 1 mM acetaldehyde, and 10 μL of a lysate of microorganisms to be measured, followed by culture at 30° C. Then, 50 μL of 10 mM DNPH was added thereto, followed by acetaldehyde-hydrazone (AcH-DNPH) labeling at 22° C. for 1 hour. The labeling reaction was stopped by addition of 3 M sodium acetate (pH 9), and a 2-fold volume of acetonitrile was added to separate a layer containing the acetaldehyde-DNPH compound dissolved therein, and then the layer was injected into HPLC and analyzed. The concentration of the labeled aldehyde was analyzed using a substance standard curve of aldehyde-DNPH (Sigma-Aldrich). As for HPLC analysis conditions, C18 column was used, and a solvent (acetonitrile and water) was allowed to flow at a flow rate of 1 ml/min, and the concentration of aldehyde was detected at a wavelength of 360 nm in an ultraviolet detector. Meanwhile, 1 unit of aldehyde dehydrogenase is designated as the concentration of acetaldehyde-DNPH reduced per minute, 1 mM, and the aldehyde dehydrogenase activity was expressed as the unit per mg of protein.

Figure 6:
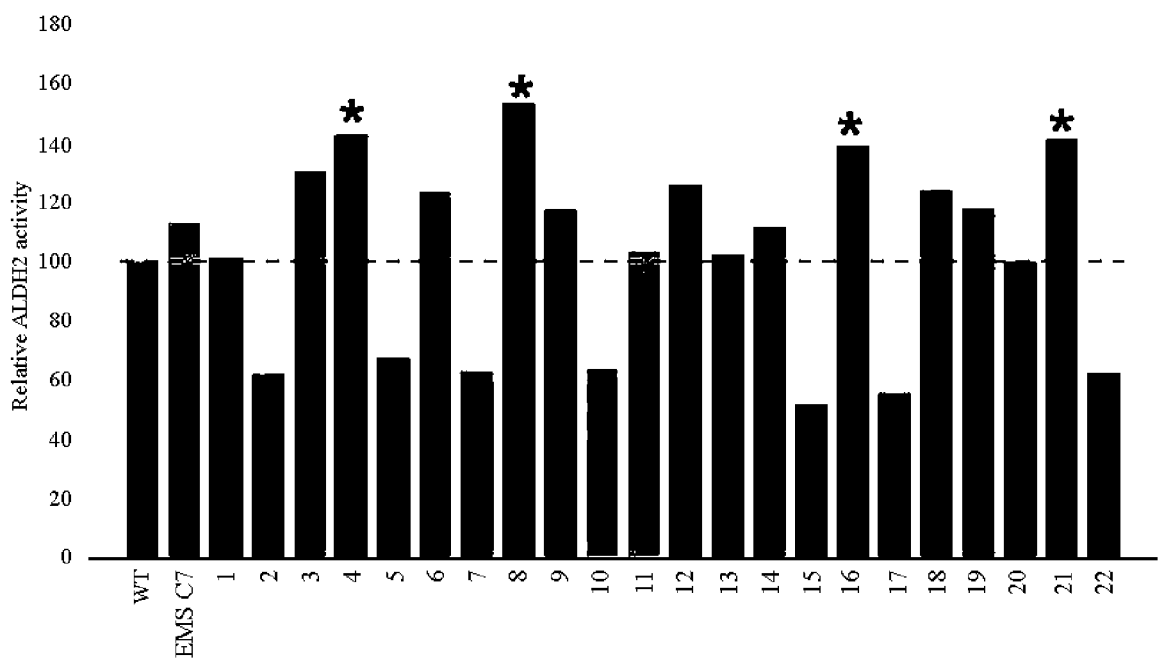
FIG. 6 is a graph showing the concentration analysis results of aldehyde dehydrogenase produced from the *Saccharomyces cerevisiae* mutant strains according to an example of the present disclosure. The numbers on the horizontal axis indicate *Saccharomyces cerevisiae* mutant strains, respectively, and the vertical axis indicates the relative aldehyde dehydrogenase activity of *Saccharomyces cerevisiae* mutant strains compared to aldehyde dehydrogenase activity of the wild *Saccharomyces cerevisiae* strain.

As a result of analyzing the concentration of aldehyde dehydrogenase, as shown in FIG. 6 below, as for the aldehyde dehydrogenase-producing ability of the lysine-resistant strains by the NTG treatment on the *Saccharomyces cerevisiae* ems c7 strain, about 42% of the lysine-resistant mutant strains showed excellent ability compared with the initial mother strain and the *Saccharomyces cerevisiae* ems c7 strain (110% excellent compared with the mother strain), and the producing ability of four species (#4, #8, #16, and #21) was enhanced by 140% or more. The four species having an excellent ability to produce aldehyde dehydrogenase showed a glutathione content of 0.9% for mutant strain #4, 0.96% for mutant strain #8, 0.93% for mutant strain #16, and 0.92% for mutant strain #21, indicating that the glutathione-producing ability was little changed by even the lysine treatment.

Table 2 shows the results of the four species of mutant strains, of which the aldehyde dehydrogenase activity was enhanced by 1.4 times or more compared with the mother strain. Based on these results, the lysine-resistant mutant *Saccharomyces cerevisiae* #8 by NTG treatment was selected as a mutant strain having an excellent ability to produce aldehyde dehydrogenase and named *Saccharomyces cerevisiae* Kwon P-1, the lysine-resistant mutant *Saccharomyces cerevisiae* #16 by NTG treatment was selected as a mutant strain having an excellent ability to produce aldehyde dehydrogenase and named *Saccharomyces cerevisiae* Kwon P-2, and the lysine-resistant mutant *Saccharomyces cerevisiae* #21 by NTG treatment was selected as a mutant strain having an excellent ability to produce aldehyde dehydrogenase and named *Saccharomyces cerevisiae* Kwon P-3.

TABLE 2

Aldehyde dehydrogenase activity of lysine-resistant mutant strains of yeas by NTG treatment

| No. | Strain name | Mutation treatment method | ALDH activity (Unit/mg-protein) |
|---|---|---|---|
| Control 1 | Saccharomyces cerevisiae WT | — | 0.10 |
| Control 2 | Saccharomyces cerevisiae ems c7 | EMS/methylglyoxal resistance | 0.11 |
| Test group 4: | Saccharomyces cerevisiae #4 | NTG/methylglyoxal and lysine resistance | 0.15 |
| Test group 8: | Saccharomyces cerevisiae #8 | NTG/methylglyoxal and lysine resistance | 0.16 |
| Test group 16: | Saccharomyces cerevisiae #16 | NTG/methylglyoxal and lysine resistance | 0.14 |
| Test group 21: | Saccharomyces cerevisiae #21 | NTG/methylglyoxal and lysine resistance | 0.14 |

Example 4

Figure 7:
FIG. 7 is a view showing optical microscopic observation results of cell morphology of the mutant strain *Saccharomyces cerevisiae* Kwon P-1 according to an example of the present disclosure.
Figure 8:
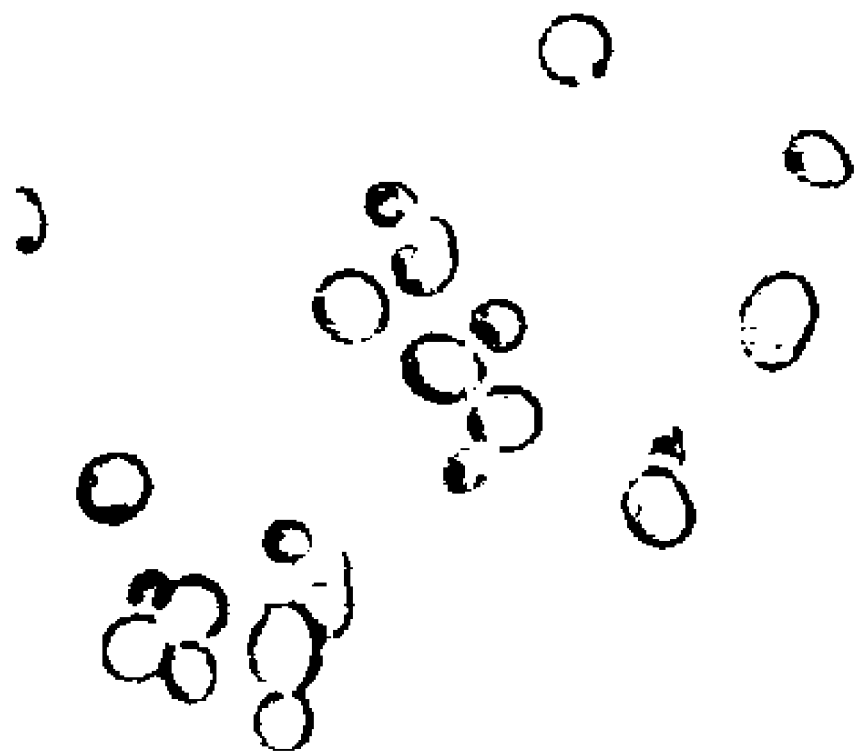
FIG. 8 is a view showing optical microscopic observation results of cell morphology of the wild *Saccharomyces cerevisiae* mutant strain according to an example of the present disclosure.

Morphological Change of Mutants Having Excellent Ability to Produce Glutathione and Aldehyde Dehydrogenase The novel mutant yeast strain having an enhanced ability to produce glutathione and aldehyde dehydrogenase were selected in Example 2-2, and for the observation of morphological changes, the mutant strain was observed using an optical microscope. The cell morphology of the mutant strain Saccharomyces cerevisiae KownP-1 is shown in FIG. 7, and the morphology of the wild yeast strain is shown in FIG. 8. The observation results by an optical microscope verified that in the mutant strain Saccharomyces cerevisiae Kwon P-1, the cell diameter increased by 60% or more and the size of vacuoles, which are organelles within the cell, were enlarged. In the example, the distinctive morphological characteristics of Saccharomyces cerevisiae Kwon P-1, in which the cell size increased by 60% and the vacuoles are large, correspond to a specialized form that can be used as an important means to prevent patent infringement and steal.

Example 5

Production of Both Glutathione and Aldehyde Dehydrogenase Using Saccharomyces cerevisiae KownP-1

Saccharomyces cerevisiae Kwon P-1 was seeded in sterilized YPD liquid media (2% peptone, 1% yeast extract, 2% glucose), and seed-cultured for 16 hours wherein the culture temperature was 30° C. and the stirring rate was 160 rpm. As for main culture, the strain was seeded at a level of 1% in sterilized YPD liquid media and cultured for 48 hours under the same conditions as in the seed culture. Thereafter, the glutathione concentration and the aldehyde dehydrogenase activity of the culture were measured. As a result of 20 times of repeated culture experiments using 20 flasks under the same conditions, the results of glutathione content and aldehyde dehydrogenase activity in the cells were obtained as shown in Table 3. The strain Saccharomyces cerevisiae Kwon P-1 can produce both glutathione and aldehyde dehydrogenase and showed 0.97% in glutathione content in cells and 0.173 unit/mg-protein in aldehyde dehydrogenase activity, referring to the average production values from 20 times of repeated experiments. These results indicate that the mutant strain Saccharomyces cerevisiae Kwon P-1 showed an increase in glutathione content by 2.3 times and an increase in aldehyde dehydrogenase activity by 1.7 times compared with the mother strain, indicating enhanced producing ability.

TABLE 3

Verification of production of both glutathione and aldehyde dehydrogenase by Saccharomyces cerevisiae Kwon P-1 through flask liquid culture

| Flask No. | Glutathione content (%) | ALDH activity (Unit/mg-protein) |
|---|---|---|
| 1 | 0.95 | 0.16 |
| 2 | 0.98 | 0.18 |
| 3 | 0.93 | 0.15 |
| 4 | 1.00 | 0.19 |
| 5 | 0.98 | 0.17 |
| 6 | 0.97 | 0.19 |
| 7 | 0.95 | 0.21 |
| 8 | 0.96 | 0.16 |
| 9 | 0.94 | 0.17 |
| 10 | 0.98 | 0.18 |
| 11 | 0.99 | 0.19 |
| 12 | 1.00 | 0.16 |
| 13 | 0.98 | 0.15 |
| 14 | 0.94 | 0.18 |
| 15 | 0.96 | 0.17 |
| 16 | 0.96 | 0.18 |
| 17 | 0.98 | 0.16 |
| 18 | 0.99 | 0.15 |
| 19 | 0.97 | 0.21 |
| 20 | 1.02 | 0.15 |
| Average | 0.972 | 0.173 |

Accession Numbers
Depository Authority: Korea Research Institute of Bioscience and Biotechnology
Accession number: KCTC13925BP
Date of deposit: 20190822
Depository institution name: Korea Research Institute of Bioscience and Biotechnology
Accession number: KCTC14122BP
Date of deposit: 20200130
Depository Authority: Korea Research Institute of Bioscience and Biotechnology
Accession number: KCTC14123BP
Date of deposit: 20200130

What is claimed is:

1. A Saccharomyces cerevisiae yeast having an enhanced ability to produce aldehyde dehydrogenase and glutathione concurrently, the Saccharomyces cerevisiae yeast is selected from the group consisting of Saccharomyces cerevisiae Kwon P-1 KCTC13925BP, Saccharomyces cerevisiae Kwon P-2 KCTC14122BP, and Saccharomyces cerevisiae Kwon P-3 KCTC14123BP,
  wherein the Saccharomyces cerevisiae yeast is obtained by a process comprising:
  a first step for treating a Saccharomyces cerevisiae yeast with ethylmethanesulfonate or nitrosoguanidine to induce mutation,
  a second step for treating the induced mutant yeast obtained in the first step with methylglyoxal to select a methylglyoxal-adapted mutant yeast from the induced mutant yeast, and
  a third step for treating the methylglyoxal-adapted mutant yeast selected in the second step with lysine to select a lysine-adapted mutant yeast from the methylglyoxal-adapted mutant yeast selected in the second step.

2. The *Saccharomyces cerevisiae* yeast according to claim 1, wherein the yeast is *Saccharomyces cerevisiae* Kwon P-1 KCTC13925BP.

3. The *Saccharomyces cerevisiae* yeast according to claim 1, wherein the yeast is *Saccharomyces cerevisiae* Kwon P-2 KCTC14122BP.

4. The *Saccharomyces cerevisiae* yeast according to claim 1, wherein the yeast is *Saccharomyces cerevisiae* Kwon P-3 KCTC14123BP.

5. The *Saccharomyces cerevisiae* yeast according to claim 1, wherein the induced mutant yeast is treated with 10 mM methylglyoxal in the second step to select the methylglyoxal-adapted mutant yeast, and wherein the methylglyoxal-adapted mutant yeast is treated with lysine at concentrations of 3% to 5% in the third step to select lysine-adapted mutant yeast.

6. A method for producing both glutathione and aldehyde dehydrogenase comprising culturing a *Saccharomyces cerevisiae* yeast of claim 1.

* * * * *